United States Patent [19]

Rosseels et al.

[11] 4,378,362
[45] Mar. 29, 1983

[54] INDOLIZINE DERIVATIVES AND PROCESS FOR PREPARING THE SAME

[75] Inventors: Gilbert Rosseels, Relegem; Henri Inion, Wemmel, both of Belgium

[73] Assignee: S.A. Labaz N.V., Brussels, Belgium

[21] Appl. No.: 232,138

[22] Filed: Feb. 6, 1981

Related U.S. Application Data

[63] Continuation-in-part of Ser. No. 207,270, Nov. 17, 1980.

[51] Int. Cl.³ .................... A61K 31/44; C07D 221/04
[52] U.S. Cl. ..................................... 424/263; 546/112
[58] Field of Search .................... 546/112; 424/263

[56] References Cited
U.S. PATENT DOCUMENTS 4,103,012 7/1978 Gubin et al. ................. 546/112

OTHER PUBLICATIONS

Noller, Textbook of Organic Chemistry, W. B. Saunders Co., Philadelphia, Pa., 1958, p. 317.

*Primary Examiner*—Henry R. Jiles
*Assistant Examiner*—Robert C. Whittenbaugh
*Attorney, Agent, or Firm*—Mason, Kolehmainen, Rathburn & Wyss

[57] ABSTRACT

Novel indolizine derivatives represented by the general formula:

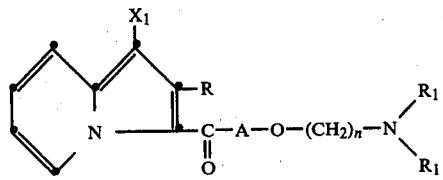

and the pharmaceutically acceptable acid addition salts thereof, wherein:

R represents an alkyl radical having from 1 to 8 carbon atoms, or a phenyl group non-substituted or bearing one or two substituents, selected from halogen atoms and from lower alkyl and alkoxy groups, $X_1$ represents hydrogen, chlorine, bromine, iodine, methyl or methoxy, A represents a group selected from:

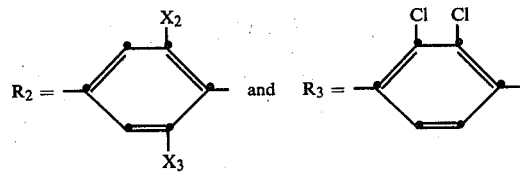

in which $X_2$ represents hydrogen, chlorine, bromine, iodine, methyl or methoxy and $X_3$ represents hydrogen, chlorine, bromine, iodine or methyl, $R_1$ represents a methyl, ethyl, n-propyl or n-butyl radical, n represents an integer in the range of 2 to 6 inclusive, with the proviso that when both $X_2$ and $X_3$ represent hydrogen or methyl, $X_1$ is other than hydrogen.

They are effective for treating pathological syndromes of the heart and particularly angina pectoris and cardiac arrhythmias.

18 Claims, No Drawings

INDOLIZINE DERIVATIVES AND PROCESS FOR PREPARING THE SAME

This application is a continuation-in-part of copending application Ser. No. 207,270 filed Nov. 17, 1980.

This invention relates to heterocyclic compounds and is concerned with novel indolizine derivatives and with a method of preparing the said novel derivatives.

The indolizine derivatives with which the present invention is concerned are the compounds represented by the general formula:

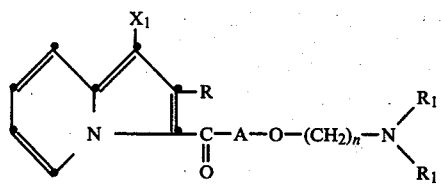

and the pharmaceutically acceptable acid addition salts thereof, for example the oxalate or hydrochloride, wherein:

R represents a branched- or straight-chain alkyl radical having from 1 to 8 carbon atoms, or a phenyl group non-substituted or bearing one or two substituents, which may be the same or different, selected from halogen atoms, for example fluorine, chlorine and bromine and from lower alkyl and alkoxy groups for example methyl and methoxy, $X_1$ represents hydrogen, chlorine, bromine, iodine, methyl or methoxy, A represents a group selected from:

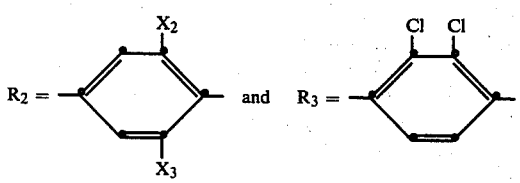

in which $X_2$ represents hydrogen, chlorine, bromine, iodine, methyl or methoxy and $X_3$ represents hydrogen, chlorine, bromine, iodine or methyl, $R_1$ represents a methyl, ethyl, n-propyl or n-butyl radical, n represents an integer in the range of 2 to 6 inclusive, with the proviso that when both $X_2$ and $X_3$ represent hydrogen or methyl, $X_1$ is other than hydrogen.

In the aforesaid general formula I, R represents, preferably, a branched- or straight-chain alkyl radical having from 1 to 8 carbon atoms, a phenyl radical, a mono-fluoro-, mono-chloro-, mono-bromo-, mono-methyl- or mono-methoxy-phenyl radical, a di-fluoro-, di-chloro-, di-bromo-phenyl radical or a methyl-phenyl radical substituted in the aromatic moiety by an atom of fluorine, chlorine or bromine. The indolizine derivatives of the invention have been found to possess useful pharmacological properties capable of rendering them of considerable value in the treatment of certain pathological syndromes of the heart, more particularly in the treatment of angina pectoris and auricular and ventricular cardiac arrhythmias of various origins.

The present invention is also concerned with pharmaceutical and veterinary compositions containing, as active principle, at least one indolizine derivative of formula I or a pharmaceutically acceptable acid addition salt thereof, in association with a pharmaceutical carrier or excipient therefor.

Another object of the present invention is to provide a process for preparing pharmaceutical or veterinary compositions whereby at least one indolizine derivative of formula I or a pharmaceutically acceptable acid addition salt thereof, is associated with a pharmaceutical carrier or excipient therefor.

Yet another object of the present invention is to provide a method of treating pathological syndromes of the heart and particularly angina pectoris and cardiac arrhythmias in a subject needing such treatment which method comprises administering to said subject an effective dose of at least one indolizine derivative of formula I or a pharmaceutically acceptable acid addition salt thereof.

Daily dosages will be preferably from 100 to 300 mg of active principle by oral route and preferably from 1 to 3 mg of active principle by parenteral route to a subject weighing 60 kgs.

The compounds of formula I can be prepared, in accordance with the invention, by condensing, in an inert solvent such as, for example benzene or toluene, a bromoalkoxy-benzoyl-indolizine of the general formula:

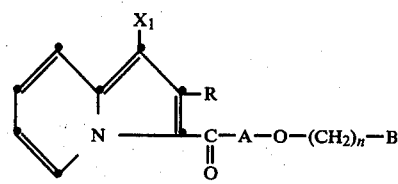

wherein $X_1$, R, A and n have the same meaning as in formula I, with a secondary amine of the general formula:

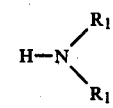

in which $R_1$ has the same meaning as in Formula I, to form the required indolizine derivative of formula I which, if desired, is reacted with an appropriate organic or inorganic acid to provide a pharmaceutically acceptable acid addition salt thereof.

The compounds of formula I may alternatively be prepared by condensing, advantageously in an aprotic solvent such as, for example, acetone, methyl ethyl ketone or toluene, an alkali metal salt, preferably the potassium or sodium salt of an appropriately substituted indolizine derivative represented by the general formula:

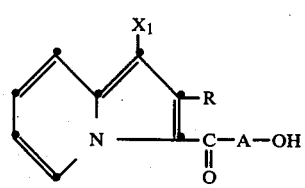

in which R, A and $X_1$ have the same meaning as in formula I, with an alkylamino derivative of the general formula:

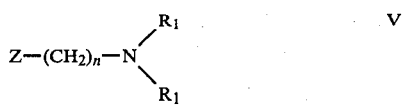

or an acid addition salt thereof, in which Z represents a halogen atom such as chlorine or bromine or a p-toluenesulphonyloxy group and n and $R_1$ have the same meaning as in formula I to give the required indolizine derivative which, if desired, is reacted with an appropriate organic or inorganic acid to provide a pharmaceutically acceptable acid addition salt thereof.

In accordance with a further aspect of the invention, the indolizine derivatives of formula I in which $X_1$ represents chlorine, bromine or iodine and A represents the group $R_3$ or a group $R_2$ in which $X_2$ represents chlorine, bromine, iodine, methyl or methoxy and $X_3$ represents chlorine, bromine, iodine or methyl can also be prepared by reacting an indolizine derivative of general formula:

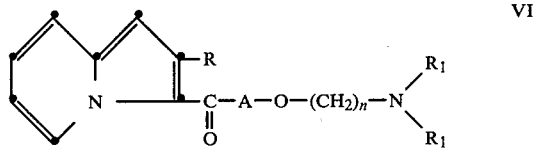

in which R, $R_1$ and n have the same meaning as in formula I and A represents the group $R_3$ or a group $R_2$ in which $X_2$ represents chlorine, bromine, iodine, methyl or methoxy and $X_3$ represents chlorine, bromine, iodine or methyl:

(a) either with N-chlorosuccinimide, the reaction taking place in a suitable medium such as dichlorethane and between 0° C. and room-temperature, to obtain the required compound of formula I in which $X_1$ represents chlorine, in free base form, (b) or with bromine or iodine, the reaction taking place at room-temperature in a suitable solvent such as dioxan and in the presence of an alkali metal acetate, for instance sodium acetate, to obtain the required compound of formula I in which $X_1$ represents bromine or iodine, in free base form, the free base so obtained being then reacted, if desired, with an organic or inorganic acid, to provide a pharmaceutically acceptable acid addition salt thereof.

The compounds of formula II can be obtained by condensing, advantageously in an inert medium such as for example acetone or methyl ethyl ketone, an alkali metal salt, preferably the potassium or sodium salt, of a compound of formula IV hereabove, with a dibromoalkane of the general formula:

in which n has the same meaning as in formula I to obtain the required compound of formula II.

The compounds of formula IV in which A represents the group $R_2$ are either compounds described in copending British patent application No. 2,051,812 A published Jan. 21, 1981 or compounds which can be prepared in accordance with methods described in the aforesaid British patent application.

The other compounds of formula IV, i.e., those in which A represents the group $R_3$ can be obtained by reacting the appropriate 2-substituted-indolizine with 2,3-dichloro-4-acetyloxy or 4-tosyloxy-benzoyl chloride. This benzoyl chloride derivative is itself prepared by acetylating 1,2-dichloro-anisole in accordance with the conditions of the FRIEDEL and CRAFTS reaction oxydating the acetyl derivative so obtained with sodium hypochlorite to form the corresponding benzoic acid derivative, demethylating with hydriodic acid in acetic acid to obtain 2,3-dichloro-4-hydroxybenzoic acid. This last-cited compound is then reacted with acetyl chloride or tosyl chloride to form the required 2,3-dichloro-4-acetyloxy or 4-tosyloxy-benzoic acid and the corresponding acyl chloride is subsequently formed in accordance with known procedures, for instance by reaction with thionyl chloride.

With respect to the compounds of formula VI, these are compounds falling within the scope of formula I above.

Indolizine derivatives are already known which have pharmacological effects capable of rendering them useful in the treatment of angina pectoris and cardiac arrhythmias.

In this connection, U.S. Pat. No. 4,103,012 can be cited which more particularly describes 2-ethyl-3-[4-(3-di-n-butylaminopropyl)-oxy-benzoyl]-indolizine known under the non-proprietary name of butoprozine. In the British patent in question, antianginal properties are attributed to compounds described therein since they produce the following cardiovascular effects:
bradycardia
decrease in arterial pressure
α-antiadrenergic effect
β-antiadrenergic effect
coronarodilating effect.

The increase of the blood-flow of the myocardium provoked by these compound is, in fact, only slight because their action does not last long: it is exerted for only a few minutes after an intravenous injection.

Furthermore, the compounds described in the aforesaid British patent only possess a weak β-adrenergic antagonist action. This action is only slight at the minimum dose at which the other four cardiovascular effects cited above manifest themselves to a significant degree.

It has now been found quite surprisingly that by substituting in an appropriate manner with one or more methyl or methoxy groups or halogen atoms for example chlorine, bromine or iodine, dialkylaminoalkyloxy-benzoyl indolizine derivatives, compounds are obtained which present a much broader spectrum of cardiovascular properties then the derivatives of U.S. Pat. No. 4,103,012 while showing less toxicity.

Thus, it has been possible to demonstrate that the indolizine derivatives of the invention can be regarded as powerful coronarodilators since they are capable of increasing the blood-flow to the myocardium to a marked degree and for a longer period of time than butoprozine. Compounds of the invention were also found to reduce cardiac frequency and arterial pressure in the animal.

Furthermore, the indolizine derivatives present a β-antiadrenergic effect which is much more powerful than that of the derivatives of the aforesaid British patent. At the minimum dose required to produce bradycardia, a reduction in arterial pressure, α-antiadrenergic and coronarodilatory effects to a significant degree, the β-antiadrenergic effect is, in fact, only slight in the case of the derivatives of the British patent in question whereas it is much stronger with the indolizine derivatives of the invention.

Moreover, the compounds of the invention reduce the consumption of oxygen by the myocardium calculated by multiplying the difference between the arterial and venous blood in oxygen by the coronary blood-flow. Thus, the compounds of the invention cause a considerable reduction in the arterio-venous difference which induces a decrease in the consumption of oxygen in spite of the increase of the coronary blood-flow.

Furthermore, unlike butoprozine, these beneficial effects on the consumption of oxygen are obtained with the compounds of the invention without any decrease in the contractility of the myocardium.

It has been further demonstrated that the derivatives of the invention are less toxic than the compounds of U.S. Pat. No. 4,103,012. Acute toxicity tests carried out by intravenous and oral routes in the animal have shown that the lethal doses are higher in the case of compounds of the invention than in the case of derivatives of the British patent in question.

Furthermore, higher blood levels can be obtained with compounds of the invention than with butoprozine.

Thus, it has been shown that the same oral dose of 1-bromo-2-methyl-3-[4-(3-di-n-butylaminopropyl)-oxy-3-bromo-benzoyl]-indolizine and of butoprozine administered to the dog induces a blood level which is three times higher with the compound of the invention than with butoprozine. Likewise, the compounds of the invention, when administered in long-term treatment per os in the dog have shown no cardiac toxicity as represented by ventricular arrhythmia which is not the case with butoprozine.

Finally, the indolizine derivatives of the invention exert a milder depressant action on the contractility of the myocardium than does butoprozine.

In man, an attack of angina pectoris is the painful consequence of a deficiency between the supply and the requirement in oxygen of the myocardium.

A compound can thus be active in the treatment of angina pectoris either by increasing the supply of oxygen or by decreasing the need of oxygen. Amongst the products commonly used in humans for treating angina pectoris, can be cited dipyridamole amongst the coronarodilators and amiodarone amongst the compounds which decrease the consumption of oxygen by the myocardium.

Comparative tests have, however, shown that the compounds of the invention are very superior to dipyridamole and amiodarone from several points of view.

In particular, it has been shown that dipyridamole does not decrease the consumption of oxygen by the myocardium and that amiodarone cannot be regarded as a coronarodilator.

The derivatives of the present invention exert their effect through both of these factors. Thus, they decrease the consumption of oxygen by the myocardium through their metabolic effects and also increase the coronary blood-flow in a long-lasting manner. Moreover, they are capable of preventing or curing not only arrhythmias induced by ischemia of the myocardium but also the auricular and ventricular arrhythmias of widely varying origins.

Thus, it appears that the halogenating, methoxylating or methylating of indolizine derivatives of U.S. Pat. No. 4,103,012 gives rise to compounds possessing a novel spectrum of pharmacological properties valuable in the treatment of cardiac deficiencies.

For instance:

the sites of the myocardium which are insufficiently irrigated can be nourished by means of the coronarodilating effect which can induce the development of an additional collateral circulation. This effect is valuable for the treatment of both anginal pain and the disturbances of rhythm consequent upon ischemia of the myocardium.

the antiadrenergic effect is also valuable for the treatment of both angina pectoris and cardiac arrhythmia in view of the important role played by hyperactivity of the sympathetic system in the etiology of these two cardiac diseases.

Since the physiological mediator of the sympathetic system is epinephrine, a compound which inhibits all the effects of epinephrine will probably be more active than a compound which only inhibits a part of these effects.

For this reason, the compounds of the present invention which inhibit both α and β effects of epinephrine present an advantage over the derivatives of the U.S. Pat. No. 4,103,012 which practically only inhibit the α effects at the minimum dose at which the other pharmacological cardiovascular effects occur.

Amongst the compounds of the invention which have shown the most outstanding anti-anginal potentialities, the following may be cited:

1-Bromo-2-methyl-3-[4-(3-di-n-butylaminopropyl)-oxy-3-bromo-benzoyl]indolizine 2-n-Butyl-3-[4-(3-di-n-butylaminopropyl)-oxy-3-bromo-benzoyl]-indolizine 2-Ethyl-3-[4-(3-di-n-butylaminopropyl)-oxy-3-chloro-benzoyl]-indolizine 2-n-Butyl-3-[4-(3-di-n-butylaminopropyl)-oxy-3-chloro-benzoyl]-indolizine 2-Isopropyl-3-[4-(3-di-n-butylaminopropyl)-oxy-3,5-dichloro-benzoyl]-indolizine 1-Bromo-2-phenyl-3-[4-(3-di-n-butylaminopropyl)-oxy-3-chloro-benzoyl]-indolizine 1-Chloro-2-ethyl-3-[4-(3-di-n-butylaminopropyl)-oxy-3-chloro-benzoyl]-indolizine 1-Chloro-2-n-butyl-3-[4-(3-di-n-butylaminopropyl)-oxy-benzoyl]-indolizine 1-Bromo-2-(4-chloro-phenyl)-3-[4-(3-di-n-butylaminopropyl)-oxy-3-chlorobenzoyl]-indolizine these compounds being in the form of the free base or of a pharmaceutically acceptable acid addition salt such as, for example, the hydrochloride or acid oxalate.

The results of pharmacological tests carried out in order to determine the cardiovascular properties of the compounds of the invention are given hereunder.

I. Antianginal properties

1. Effect on blood-flow to the myocardium.

This test was carried out in accordance with the technique described by R. CHARLIER & J. BAUTHIER in Arzneimittel—Forschung "Drug Research" 23, No. 19, 1305–1311 (1973).

It was undertaken on anaesthetized dogs which received the substance under study by intravenous route. The intensity of the maximum effect on blood-flow to the myocardium was expressed in percentage of the corresponding value before injection. The time required for the maximum effect to decrease by 50% represented the duration of the effect. This time was measured in minutes.

The following results were registered:

$$\text{structure: pyridine-CH=C(R)-C(=O)-C}_6\text{H}_2(X_2)(X_3)(X_1)\text{-O-(CH}_2)_n\text{-NR}_1\text{R}_1$$

| $X_1$ | $X_2$ | $X_3$ | R | $R_1$ | n | Dose (mg/kg) | Max. increase (%) | Time required to decrease to 50% |
|---|---|---|---|---|---|---|---|---|
| Br | Br | H | $C_2H_5$ | $n$-$C_4H_9$ | 3 | 10 | 60 | 90 |
| Br | Br | H | $CH_3$ | $n$-$C_4H_9$ | 3 | 10 | 125 | 40 |
| Br | Br | H | $n$-$C_4H_9$ | $n$-$C_3H_7$ | 3 | 10 | 100 | 20 |
| Br | Br | H | $n$-$C_3H_7$ | $n$-$C_3H_7$ | 3 | 10 | 90 | 20 |
| Br | Br | H | phenyl | $n$-$C_3H_7$ | 3 | 10 | 100 | 20 |
| Br | Br | H | 4-Br-phenyl | $n$-$C_4H_9$ | 3 | 10 | 150 | 100 |
| H | Br | H | 4-Br-phenyl | $n$-$C_4H_9$ | 3 | 10 | 90 | 25 |
| Br | Br | H | $CH_3$ | $n$-$C_4H_9$ | 3 | 10 | 77 | 45 |
| H | Br | H | $n$-$C_3H_7$ | $n$-$C_4H_9$ | 3 | 2 | 120 | 25 |
| H | Br | H | $n$-$C_4H_9$ | $n$-$C_4H_9$ | 3 | 5 | 70 | 60 |
| Br | Cl | H | iso-$C_3H_7$ | $n$-$C_4H_9$ | 3 | 5 | 133 | 20 |
| Cl | H | H | $n$-$C_4H_9$ | $n$-$C_4H_9$ | 3 | 10 | 60 | 30 |
| H | Cl | Cl | iso-$C_3H_7$ | $n$-$C_4H_9$ | 3 | 10 | 30 | 75 |
| H | Cl | Cl | 4-Br-phenyl | $n$-$C_4H_9$ | 3 | 10 | 45 | 15 |
| H | Cl | Cl | iso-$C_3H_7$ | $n$-$C_4H_9$ | 3 | 10 | 30 | 75 |
| H | Cl | H | 4-Br-phenyl | $n$-$C_4H_9$ | 3 | 10 | 30 | 45 |
| H | Cl | H | 4-Br-phenyl | $n$-$C_3H_7$ | 3 | 8 | 45 | 25 |
| H | Cl | H | iso-$C_3H_7$ | $n$-$C_3H_7$ | 3 | 5 | 80 | 90 |
| Br | Cl | H | phenyl | $n$-$C_4H_9$ | 3 | 10 | 90 | 90 |
| Br | Cl | H | $n$-$C_4H_9$ | $n$-$C_3H_7$ | 3 | 10 | 40 | 90 |
| Br | Cl | H | 4-Br-phenyl | $n$-$C_3H_7$ | 3 | 10 | 50 | 50 |
| H | Cl | H | $n$-$C_4H_9$ | $n$-$C_3H_7$ | 3 | 5 | 75 | 30 |
| H | Cl | H | $C_2H_5$ | $n$-$C_4H_9$ | 3 | 6 | 70 | 45 |
| Br | Cl | H | 4-Cl-phenyl | $n$-$C_3H_7$ | 3 | 10 | 63 | 45 |
| H | Cl | H | 4-Br-phenyl | $n$-$C_4H_9$ | 3 | 10 | 60 | 25 |
| Br | Cl | H | $n$-$C_3H_7$ | $n$-$C_4H_9$ | 3 | 2.5 | 50 | 60 |
| Cl | Cl | H | 4-Br-phenyl | $n$-$C_3H_7$ | 3 | 8 | 70 | 90 |
| Cl | Cl | H | $C_2H_5$ | $n$-$C_4H_9$ | 3 | 1 | 40 | 15 |
| Cl | Cl | H | $C_2H_5$ | $n$-$C_3H_7$ | 3 | 3.3 | 60 | 25 |
| Cl | H | H | 4-Cl-phenyl | $n$-$C_3H_7$ | 3 | 5 | 50 | 40 |
| Butoprozine | | | | | | 10 | 120 | 4 |
| Amiodarone | | | | | | 10 | 36 | 7 |

These results clearly show that the compounds of the invention are more valuable than butoprozine and amiodarone as regards the effects on bloodflow to the myocardium.

2. Antiadrenergic effects

The purpose of this test was to determine the capacity of the compounds under study to reduce epinephrine-increased blood-pressure (anti-$\alpha$ effect) and epinephrine-accelerated heart rate (anti-$\beta$ effect) in the dog previously anaesthetized with pentobarbital and atropinized.

Anti-$\alpha$ effect

For each dog, the dose of epinephrine was first determined which provoked a reproducible increase by about 100 mm. Hg in the arterial pressure (between 5 and 10 μg/kg).

After that, the dose of epinephrine so determined was administered followed by a dose by intravenous route of the compound to be studied. The percentage of reduction of the hypertension provoked by the compound under study in comparison with the hypertension previously obtained (about 100 mm.Hg) was then registered.

Anti-$\beta$ effect

During the same test as that described above, the epinephrine provoked a reproducible increase in the heart-rate of about 70 beats/min. The percentage of reduction of the epinephrine-induced acceleration of heart-rate produced by the compound under study in comparison with the tachycardia previously measured (about 70 beats) was then registered. In both cases, the results were expressed as follows:

+ for a <50%-reduction of the increase in pressure or cardiac frequency

++ for a ≧50%-reduction of the increase in pressure or cardiac frequency

+++ for a subtotal reduction of the increase in pressure or cardiac frequency

The following results were registered:

| $X_1$ | $X_2$ | $X_3$ | R | $R_1$ | n | Dose (mg/kg) | Anti-α effect | Anti-β effect |
|---|---|---|---|---|---|---|---|---|
| Br | Br | H | $C_2H_5$ | n-$C_4H_9$ | 3 | 10 | ++++++ | |
| Br | H | H | $C_2H_5$ | n-$C_4H_9$ | 3 | 6 | +++++ | |
| Br | Br | H | —⟨C₆H₄⟩—F | n-$C_4H_9$ | 3 | 10 | +++++ | |
| Br | Br | Br | n-$C_3H_7$ | n-$C_3H_7$ | 3 | 10 | ++++++ | |
| H | Br | H | —⟨C₆H₅⟩ | n-$C_4H_9$ | 3 | 10 | +++++ | |
| H | Br | H | $C_2H_5$ | n-$C_4H_9$ | 3 | 7.5 | +++++ | |
| H | Br | H | n-$C_4H_9$ | n-$C_4H_9$ | 3 | 5 | +++++ | |
| H | Br | H | n-$C_4H_9$ | n-$C_3H_7$ | 3 | 5 | +++++ | |
| Br | Br | H | $CH_3$ | n-$C_4H_9$ | 3 | 5 | +++++ | |
|  |  |  |  |  |  | 10 | ++++++ | |
| H | Br | H | n-$C_4H_9$ | n-$C_4H_9$ | 3 | 5 | +++++ | |
|  |  |  |  |  |  | 10 | ++++++ | |
| H | Br | H | iso-$C_3H_7$ | n-$C_4H_9$ | 3 | 6 | +++++ | |
| Cl | H | H | n-$C_4H_9$ | N-$C_4H_9$ | 3 | 10 | +++++ | |
| Cl | H | H | n-$C_3H_7$ | n-$C_4H_9$ | 3 | 7.5 | ++++++ | |
| H | Cl | H | n-$C_4H_9$ | n-$C_4H_9$ | 3 | 10 | +++++ | |
| H | Cl | H | $C_2H_5$ | n-$C_3H_7$ | 3 | 10 | ++ | ++ |
| H | Cl | H | $C_2H_5$ | n-$C_4H_9$ | 3 | 6 | ++++ | |
| H | Cl | Cl | iso-$C_3H_7$ | n-$C_4H_9$ | 3 | 10 | ++ | ++ |
| H | Cl | H | —⟨C₆H₄⟩—Br | n-$C_4H_9$ | 3 | 10 | ++ | ++ |
| H | Cl | H | iso-$C_3H_7$ | n-$C_3H_7$ | 3 | 10 | ++ | ++ |
| Br | Cl | H | —⟨C₆H₅⟩ | n-$C_4H_9$ | 3 | 10 | ++ | +++ |
| Br | Cl | H | $C_2H_5$ | n-$C_3H_7$ | 3 | 7.8 | ++ | ++ |
| Br | Cl | H | —⟨C₆H₄⟩—Br | n-$C_3H_7$ | 3 | 10 | ++ | ++ |
| Br | Cl | H | n-$C_4H_9$ | n-$C_3H_7$ | 3 | 10 | ++ | + |
| Br | Cl | H | n-$C_4H_9$ | n-$C_4H_9$ | 3 | 10 | ++ | ++ |
| Br | Cl | H | —⟨C₆H₄⟩—Cl | n-$C_3H_7$ | 3 | 10 | ++ | ++ |
| Br | Cl | H | —⟨C₆H₄⟩—Br | n-$C_3H_7$ | 3 | 10 | ++ | ++ |
| Br | Cl | H | $C_2H_5$ | n-$C_4H_9$ | 3 | 10 | +++++ | |
| Br | Cl | H | —⟨C₆H₄⟩—Cl | n-$C_3H_7$ | 3 | 10 | +++++ | |
| H | Cl | H | —⟨C₆H₄⟩—Br | n-$C_4H_9$ | 3 | 10 | ++ | + |
| Br | Cl | H | —⟨C₆H₄⟩—Br | n-$C_3H_7$ | 3 | 10 | +++++ | |

-continued

| $X_1$ | $X_2$ | $X_3$ | R | $R_1$ | n | Dose (mg/kg) | Anti-α effect | Anti-β effect |
|---|---|---|---|---|---|---|---|---|
| Br | Cl | H | n-$C_3H_7$ | n-$C_4H_9$ | 3 | 10 | +++++ | |
| Cl | Cl | H | phenyl-Br | n-$C_3H_7$ | 3 | 8 | ++++ | |
| Cl | Cl | H | $C_2H_5$ | n-$C_4H_9$ | 3 | 0.5 | ++++ | |
| Cl | Cl | H | $C_2H_5$ | n-$C_3H_7$ | 3 | 3.3 | ++++++ | |
| Cl | H | H | phenyl-Cl | n-$C_4H_9$ | 3 | 10 | +++++ | |
| Cl | H | H | phenyl-Cl | n-$C_3H_7$ | 3 | 5 | ++ + | |
| Cl | H | H | phenyl | n-$C_4H_9$ | 3 | 5 | ++++++ | |
| H | Br | H | iso-$C_3H_7$ | n-$C_3H_7$ | 3 | 7.5 | +++++ | |
| Br | $OCH_3$ | H | $CH_3$ | n-$C_3H_7$ | 3 | 7.5 | ++ | ++ |
| Cl | Cl | Cl | $C_2H_5$ | n-$C_3H_7$ | 3 | 10 | ++ | ++ |
| Cl | Cl | Cl | phenyl | n-$C_4H_9$ | 3 | 10 | +++++ | |
| Cl | Br | H | $C_2H_5$ | n-$C_4H_9$ | 3 | 10 | ++++++ | |
| Cl | Br | Br | phenyl | n-$C_3H_7$ | 3 | 10 | + | + |
| Br | Cl | Cl | phenyl | n-$C_3H_7$ | 3 | 10 | ++ | ++ |
| Br | Cl | Cl | phenyl | n-$C_4H_9$ | 3 | 10 | ++ | ++ |
| Br | $CH_3$ | $CH_3$ | $CH_3$ | n-$C_4H_9$ | 3 | 10 | +++++ | |
| H | Br | Br | phenyl-Br | n-$C_3H_7$ | 3 | 10 | ++++++ | |
| H | Br | Br | phenyl | n-$C_4H_9$ | 3 | 10 | ++ | ++ |
| $OCH_3$ | Cl | H | phenyl | n-$C_3H_7$ | 3 | 10 | ++++++ | |
| $OCH_3$ | $OCH_3$ | H | phenyl | n-$C_3H_7$ | 3 | 10 | ++ | ++ |
| H | $OCH_3$ | H | $C_2H_5$ | n-$C_4H_9$ | 3 | 10 | +++++ | |
| Br | $OCH_3$ | H | $C_2H_5$ | n-$C_4H_9$ | 3 | 5 | ++ | ++ |
| Br | $OCH_3$ | H | $CH_3$ | n-$C_4H_9$ | 3 | 7 | ++ | ++ |
| Br | $OCH_3$ | H | $CH_3$ | n-$C_3H_7$ | 3 | 7.5 | ++ | ++ |
| Butoprozine | | | | | | 5 | +++ | + |
| Amiodarone | | | | | | 10 | ++ | ++ |

These results again show that the compounds of the invention are more valuable than those of the prior art.

II. Anti-arrhythmic properties

These properties were demonstrated after administration of the compound under study by intragastric route to mice using the LAWSON test (J. Pharmac. Exp. Therap. 1968, 160 (1) p. 22–31).

The arrhythmia was provoked by making the animals inhale chloroform to total asphyxia and by later observing the ventricular rhythm. The dose of compound protecting 50% of the animals against ventricular fibrillation i.e. the $AD_{50}$ was then recorded. The following results were registered:

| $X_1$ | $X_2$ | $X_3$ | R | $R_1$ | n | $AD_{50}$ (mg/kg) |
|---|---|---|---|---|---|---|
| Br | Br | H | $CH_3$ | n-$C_4H_9$ | 3 | 180 |
| H | Br | H | n-$C_4H_9$ | n-$C_4H_9$ | 3 | 170 |
| Butoprozine | | | | | | 270 |

III Toxicity

Acute toxicity

Acute toxicity tests were carried out on rats and mice. The following results were registered in comparison with butoprozine. The compounds of the invention were used in oxalate acid form except those marked (x) which were tested in hydrochloride form.

| $X_1$ | $X_2$ | $X_3$ | R | $R_1$ | n | $LD_{50}$ (mg/kg) |
|---|---|---|---|---|---|---|
| (a) By intravenous route to rats | | | | | | |
| (*) Br | Br | H | $CH_3$ | n-$C_4H_9$ | 3 | 70 |
| H | Br | H | n-$C_4H_9$ | n-$C_4H_9$ | 3 | 60 |
| (*) H | Cl | H | $C_2H_5$ | n-$C_4H_9$ | 3 | 65 |
| H | Cl | Cl | iso-$C_3H_7$ | n-$C_4H_9$ | 3 | >100 |
| (*) Br | Cl | H | ⟨phenyl⟩ | n-$C_4H_9$ | 3 | >100 |
| (*) H | Cl | H | n-$C_4H_9$ | n-$C_4H_9$ | 3 | >50 ($LD_0$ >50 mg/kg) |
| Cl | Cl | H | $C_2H_5$ | n-$C_4H_9$ | 3 | 50 |
| Cl | H | H | n-$C_4H_9$ | n-$C_4H_9$ | 3 | 50 |
| Br | Cl | H | ⟨phenyl-Cl⟩ | n-$C_4H_9$ | 3 | >100 ($LD_0$ >100 mg/kg) |
| Butoprozine | | | | | | 22 |
| (b) By intravenous route to mice | | | | | | |
| (*) Br | Br | H | $CH_3$ | n-$C_4H_9$ | 3 | 50 |
| Butoprozine | | | | | | 25 |
| (c) By intragastric route to mice | | | | | | |
| (*) Br | Br | H | $CH_3$ | n-$C_4H_9$ | 3 | >5000 ($LD_0$ >5000 mg/kg) |
| Butoprozine | | | | | | 1600 |

These results show that the compounds of the invention are far less toxic than butoprozine.

Cardiac tolerance and general toxicity in long-term toxicity tests

1-Bromo-2-methyl-3-[4-(3-di-n-butylaminopropyl)-oxy-3-bromo-benzoyl]-indolizine hydrochloride, 2-n-butyl-3-[4-(3-di-n-butylaminopropyl)-oxy-3-bromo-benzoyl]-indolizine hydrochloride and 2-n-butyl-3-[4-(3-di-n-butylaminopropyl)-oxy-3-chloro-benzyl]-indolizine hydrochloride provoked neither ventricular arrhythmia nor mortality at the dose of 200 mg/kg/day by oral route in the dog.

As against this, butoprozine was found to provok ventricular arrhythmia with a dose as low as 50 mg/kg/day by oral route in the dog, the lethal dose of this compound being between 50 and 100 mg/kg/day.

It will be appreciated that for therapeutic use the compounds of the invention will normally be administered in the form of a pharmaceutical or veterinary composition, which may be in a dosage unit form appropriate to the desired mode of administration.

Thus the pharmaceutical or veterinary composition may be in a dosage unit form suitable for oral administration, for example a coated or uncoated tablet, a hard- or soft-gelatin capsule, a packaged powder, or a discrete amount of a suspension, or a syrup. The composition may alternatively take the form of a suppository for rectal administration, or of a solution or suspension for parenteral administration.

When in dosage unit form, the composition may contain for example from 15% to 50% by weight of the active ingredient per dosage unit for oral administration, from 3% to 15% of the active ingredient per dosage unit for rectal administration and from 3% to 5% of the active ingredient per dosage unit for parenteral administration.

Irrespective of the form which the composition takes, the pharmaceutical or veterinary composition of the invention will normally be prepared by associating at least one of the compounds of formula I or a pharmaceutically acceptable acid addition salt thereof with an appropriate pharmaceutical carrier or excipient therefor, for example one or more of the following substances: milk sugar, starches, talc, magnesium stearate, polyvinylpyrrolidone, alginic acid, colloidal silica, distilled water, benzyl alcohol or flavouring agents.

The following Examples illustrate the invention:

EXAMPLE 1

1-Bromo-2-ethyl-3-[4-(3-di-n-propylaminopropyl)-oxy-3-bromo-benzoyl]-indolizine and its acid oxalate (a) 1-Bromo-2-ethyl-3-[4-(3-bromopropyl)-oxy-3-bromo benzoly]-indolizine A mixture of 7.7 g (0.018 mol) of 1-bromo-2-ethyl-3-(3-bromo-4-hydroxybenzoyl) indolizine, 5 g (0.036 mol) of anhydrous potassium carbonate and 50 ml of methyl ethyl ketone was stirred in a flask for 30 minutes. To this reaction medium 14.4 g (0.072 mol) of 1,3-dibromo-propane were then added and the mixture was refluxed for 20 hours. After cooling, the mineral salts were filtered out and washed with acetone. The solvents were evaporated off together with the 1,3-dibromo-propane in excess. In this manner, 13.2 g of a product were obtained which were purified by elution chromatography on silica using benzene as elution agent. A first fraction of an unknown product was obtained and then a second fraction of 8 g of the desired product.

In this manner, 1-bromo-2-ethyl-3-[4-(3-bromo-propyl)-oxy-3-bromo-benzoyl]-indolizine was obtained in a yield of 83.6%.

M.P.: 105°–106° C.

(b) 1-Bromo-2-ethyl-3-[4-(3-di-n-propylaminopropyl)-oxy-3-bromo-benzoyl]indolizine A mixture of 2.2 g (0.004 mol) of 1-bromo-2-ethyl-3-[4-(3-bromopropyl)-oxy-3-bromo-benzoyl]-indolizine, 1.2 g (0.012 mol) of di-n-propylamine and 25 ml of toluene were refluxed in a flask for 20 hours. After cooling, the reaction medium was washed twice with 10 ml of water and the solvent was evaporated off under vacuum. Thus, 2.5 g of a residue were obtained which were purified by elution chromatography on silica using ethyl acetate as eluent. By this method, 2.4 g of 1-bromo-2-ethyl-3-[4-(3-di-n-propylaminopropyl)-oxy-3-bromo-benzoyl]-indolizine in free base form were obtained.

(c)

1-Bromo-2-ethyl-3-[4-(3-di-n-propylaminopropyl)-oxy-3-bromo-benzoyl]-indolizine acid oxalate.

The base previously obtained was dissolved in 30 ml of ethyl ether and then reacted with 0.55 g of oxalic acid in 70 ml of ethyl ether to give 2.4 g of the desired salt in crude form. From this quantity, 2.0 g of pure 1-bromo-2-ethyl-3-[4-(3-di-n-propylaminopropyl)-oxy-3-bromo-benzoyl]-indolizine acid oxalate were obtained by recristallization from 75 ml of isopropanol.

Yield: 75%
M.P.: 139°–140° C.

EXAMPLE 2

1-Bromo-2-methyl-3-[4-(3-di-n-butylaminopropyl)-oxy-3-bromo-benzoyl]indolizine and salts thereof.

Into a 1-l flask, a mixture of 180 ml of water, 180 ml of toluene, 73 g (0.178 mol) of 1-bromo-2-methyl-3-(3-bromo-4-hydroxy-benzoyl)-indolizine, 42.7 g (0.21 mol) of 1-di-n-butylamino-3-chloro-propane and 34.5 g of potassium carbonate was introduced while stirring. The reaction medium was heated under reflux for 20 hours. After cooling to room-temperature, the aqueous phase was decanted and the toluene layer was washed three times, each time with 200 ml of water. The toluene solution was transferred to a flask and, under atmospheric pressure, toluene was distilled off to dryness and the residue so obtained was cooled. In this manner, crude 1-bromo-2-methyl-3-[4-(3-di-n-butylaminopropyl)-oxy-3-bromo-benzoyl]-indolizine was obtained in free base form. The following salts of this compound were then prepared:

(a) hydrochloride

To the free base previously obtained, a solution of 8 g of hydrochloric acid in 61 ml of ethyl acetate was added. The precipitate so formed, i.e. 104 g, was suction-filtered, washed with ethyl acetate and recrystallized from 500 ml of isopropanol. In this manner, 93 g of 1-bromo-2-methyl-3-[4-(3-di-n-butylaminopropyl)-oxy-3-bromo-benzoyl]-indolizine hydrochloride were obtained.

Yield: 84.7% M.P.: 172° C.

(b) acid oxalate

To an ethereal solution of the base previously obtained, an equimolecular solution of oxalic acid in ethyl ether was added. The salt so obtained was recrystallized from isopropanol.

In this manner, 1-bromo-2-methyl-3-[4-(3-di-n-butylaminopropyl)-oxy-3-bromo-benzoyl]-indolizine acid oxalate was obtained.

M.P.: 89°–90° C.

EXAMPLE 3

2-Methyl-3-[4-(3-di-n-butylaminopropyl)-oxy-3,5-dibromo-benzoyl]-indolizine acid oxalate Into a 250 ml-flask, a mixture of 4 g (0.01 mol) of 2-methyl-3-(3,5-dibromo-4-hydroxy-benzoyl)-indolizine and 150 ml of acetone was introduced. After the indolizine dissolved, there were added 4 g of anhydrous potassium carbonate and 2.2 g of di-n-butylaminopropyl chloride.

While stirring, the reaction mixture was refluxed for 16 hours. After cooling to room-temperature, the mineral salts were filtered out and washed with acetone on the filter. The acetone was then distilled off under reduced pressure using a rotatory evaporator and the oily residue was dissolved in about 100 ml of ethyl acetate. The medium was filtered on a filter and 1.5 g of anhydrous oxalic acid was added to the filtrate. The reaction medium was allowed to stand and the oxalate which crystallized was filtered out, washed on the filter with ethyl acetate and dried under vacuum.

In this manner, 6.2 g of 2-methyl-3-[4-(3-di-n-butylaminopropyl)-oxy-3,5-dibromo-benzoyl]-indolizine acid oxalate were obtained.

Yield: 92.7%
M.P.: 96° C.

EXAMPLE 4

1-Bromo-2-ethyl-3-[4-(3-di-n-propylaminopropyl)-oxy-3,5-dichloro-benzoyl]-indolizine acid oxalate Into a 250 ml flask were introduced 2.8 g (0.005 mol) of 2-ethyl-3-[4-(3-di-n-propylaminopropyl)-oxy-3,5-dichloro-benzoyl]-indolizine acid oxalate and 80 ml of dioxan. The reaction mixture was stirred and after the indolizine had dissolved, 0.8 g of anhydrous sodium acetate was added. Through a dropping-funnel was added, dropwise and under vigorous stirring, a solution of 0.8 g of bromine in 20 ml of dioxan. The temperature was maintained at about 20° C. during the introduction of the bromine.

After the medium had been stirred for 2 hours at room-temperature, the dioxan was distilled off under vacuum with a rotatory evaporator. The solid residue was dissolved in water, made alkaline with a sodium hydroxide solution and extracted with chloroform. The chloroformic solution was washed three times with water and the chloroform was distilled off under reduced pressure. The oily residue so obtained was taken up in dry ethyl ether and after filtration on a filter the acid oxalate was formed.

In this manner, 1.8 g of 1-bromo-2-ethyl-3-[4-(3-di-n-propylaminopropyl)-oxy-3,5-dichloro-benzoyl]-indolizine acid oxalate was obtained after recrystallization from ethyl acetate.

Yield: 55.8%
M.P.: 135° C.

Using the appropriate starting-products, the following compounds were prepared by utilizing the various processes described in the foregoing Examples.

| Compounds | M.P. °C. |
|---|---|
| 1-Bromo-2-ethyl-3-[4-(3-di-n-butylaminopropyl)-oxy-benzoyl]-indolizine acid oxalate | 107–108 (isopropanol) |
| 1-Bromo-2-(4-bromo-phenyl)-3-[4-(3-di-n-butylaminopropyl)-oxy-benzoyl]-indolizine acid oxalate | 92–94 (isopropanol) |

-continued

| Compounds | M.P. °C. |
|---|---|
| 1-Chloro-2-methyl-3-[4-(3-di-n-butylaminopropyl)-oxy-benzoyl]-indolizine acid oxalate | 92–93 (isopropanol) |
| 1-Chloro-2-ethyl-3-[4-(3-di-n-propylaminopropyl)-oxy-benzoyl]-indolizine acid oxalate | 162 (isopropanol) |
| 1-Chloro-2-n-propyl-3-[4-(3-di-n-butylaminopropyl)-oxy-benzoyl]-indolizine acid oxalate | 111–112 (isopropanol) |
| 1-Chloro-2-n-butyl-3-[4-(3-di-n-butylaminopropyl)-oxy-benzoyl]-indolizine acid oxalate | 106–108 (isopropanol) |
| 1-Chloro-2-phenyl-3-[4-(3-di-n-propylaminopropyl)-oxy-benzoyl]-indolizine acid oxalate | 161–162 (isopropanol) |
| 1-Chloro-2-(4-chloro-phenyl)-3-[4-(3-di-n-butylaminopropyl)-oxy-benzoyl]-indolizine acid oxalate | 158–159 (methanol) |
| 1-Chloro-2-phenyl-3-[4-(3-di-n-butylaminopropyl)-oxy-benzoyl]-indolizine acid oxalate | 160–161 (methanol) |
| 1-Chloro-2-n-butyl-3-[4-(6-di-n-butylaminohexyl)-oxy-benzoyl]-indolizine acid oxalate | 80–82 (benzene) |
| 2-Methyl-3-[4-(3-di-n-butylaminopropyl)-oxy-3-bromo-benzoyl]-indolizine acid oxalate | 141–143 (10/1 ethyl acetate/ isopropanol) |
| 2-Ethyl-3-[4-(3-di-n-propylaminopropyl)-oxy-3-bromo-benzoyl]-indolizine acid oxalate | 163 (isopropanol) |
| 2-Ethyl-3-[4-(3-di-n-butylaminopropyl)-oxy-3-bromo-benzoyl]-indolizine acid oxalate | 98–99 (isopropanol) |
| 2-n-Propyl-3-[4-(3-di-n-propylaminopropyl)-oxy-3-bromo-benzoyl]-indolizine acid oxalate | 145 (isopropanol) |
| 2-n-Propyl-3-[4-(3-di-n-butylaminopropyl)-oxy-3-bromo-benzoyl]-indolizine acid oxalate | 113–115 (isopropanol) |
| 2-Isopropyl-3-[4-(3-di-n-butylaminopropyl)-oxy-3-bromo-benzoyl]-indolizine acid oxalate | 105–107 (benzene) |
| 2-n-Butyl-3-[4-(3-di-n-propylaminopropyl)-oxy-3-bromo-benzoyl]-indolizine acid oxalate | 136–137 (isopropanol) |
| 2-n-Butyl-3-[4-(3-di-n-butylaminopropyl)-oxy-3-bromo-benzoyl]-indolizine acid oxalate | 86–87 (isopropanol) |
| 2-Phenyl-3-[4-(3-di-n-propylaminopropyl)-oxy-3-bromo-benzoyl]-indolizine acid oxalate | 148–149 (isopropanol) |
| 2-Phenyl-3-[4-(3-di-n-butylaminopropyl)-oxy-3-bromo-benzoyl]-indolizine acid oxalate | 129–130 (isopropanol) |
| 2-(4-Fluoro-phenyl)-3-[4-(3-di-n-butylaminopropyl)-oxy-3-bromo-benzoyl]-indolizine acid oxalate | 110 (isopropanol) |
| 2-(4-Chloro-phenyl)-3-[4-(3-di-n-propylaminopropyl)-oxy-3-bromo-benzoyl]-indolizine acid oxalate | 163–164 (methanol) |
| 2-(4-Chloro-phenyl)-3-[4-(3-di-n-butylaminopropyl)-oxy-3-bromo-benzoyl]-indolizine acid oxalate | 130–140 (isopropanol) |
| 2-(3-Bromo-phenyl)-3-[4-(3-di-n-propylaminopropyl)-oxy-3-bromo-benzoyl]-indolizine acid oxalate | 142–143 (isopropanol) |
| 2-(4-Bromo-phenyl)-3-[4-(3-di-n-butylaminopropyl)-oxy-3-bromo-benzoyl]-indolizine acid oxalate | 147–148.5 (methanol) |
| 2-(4-Methoxy-phenyl)-3-[4-(3-di-n-butylaminopropyl)-oxy-3-bromo-benzoyl]-indolizine acid oxalate | 169 (isopropanol) |
| 2-Isopropyl-3-[4-(5-di-n-butylaminopentyl)-oxy-3-bromo-benzoyl]-indolizine acid oxalate | 80–82 (benzene) |

-continued

| Compounds | M.P. °C. |
|---|---|
| 2-Isopropyl-3-[4-(3-di-n-propylaminopropyl)-oxy-3-bromo-benzoyl]-indolizine acid oxalate | 179 (isopropanol) |
| 2-Methyl-3-[4-(3-di-n-butylaminopropyl)-oxy-3-chloro-benzoyl]-indolizine acid oxalate | 141–143 (isopropanol) |
| 2-Ethyl-3-[4-(3-di-n-propylaminopropyl)-oxy-3-chloro-benzoyl]-indolizine acid oxalate | 161–162 (methanol) |
| 2-Ethyl-3-[4-(3-di-n-butylaminopropyl)-oxy-3-chloro-benzoyl]-indolizine acid oxalate | 116–117 (isopropanol) |
| 2-Isopropyl-3-[ 4-(3-di-n-butylaminopropyl)-oxy-3-chloro-benzoyl]-indolizine acid oxalate | 115–117 (isopropanol) |
| 2-Isopropyl-3-[4-(3-di-n-propylaminopropyl)-oxy-3-chloro-benzoyl]-indolizine acid oxalate | 168–169 (methanol) |
| 2-n-Butyl-3-[4-(3-di-n-butylaminopropyl)-oxy-3-chloro-benzoyl]-indolizine acid oxalate | 84–85 and 107–109 (isopropanol) |
| 2-n-Butyl-3-[4-(3-di-n-propylaminopropyl)-oxy-3-chloro-benzoyl]-indolizine acid oxalate | 130–131 (isopropanol) |
| 2-Phenyl-3-[2-Phenyl-3-[4-(3-di-n-butylaminopropyl)-oxy-3-chloro-benzoyl]-indolizine acid oxalate | 121–122 (isopropanol) |
| 2-Phenyl-3-[4-(3-di-n-propylaminopropyl)-oxy-3-chloro-benzoyl]-indolizine acid oxalate | 157–159 (methanol) |
| 2-(4-Methyl-phenyl)-3[4-(3-di-n-propylaminopropyl)-oxy-3-chloro-benzoyl]-indolizine acid oxalate | 134–135 (isopropanol) |
| 2-(4-Bromo-phenyl)-3-[4-(3-di-n-propylaminopropyl)-oxy-3-chloro-benzoyl]-indolizine acid oxalate | 154–155 (methanol) |
| 2-(4-Bromo-phenyl)-3-[4-(3-di-n-butylaminopropyl)-oxy-3-chloro-benzoyl]-indolizine acid oxalate | 134–135 (isopropanol) |
| 2-(3-Bromo-phenyl)-3-[4-(3-di-n-butylaminopropyl)-oxy-3-chloro-benzoyl]-indolizine acid oxalate | 92–93 (isopropanol) |
| 2-(3-Bromo-phenyl-3-[4-(3-di-n-propylaminopropyl)-oxy-3-chloro-benzoyl]-indolizine acid oxalate | 148–150 (isopropanol) |
| 2-(4-Chloro-phenyl)-3-[4-(3-di-n-butylaminopropyl)-oxy-3-chloro-benzoyl]-indolizine acid oxalate | 116–118 (isopropanol) |
| 2-(4-Chloro-phenyl)-3-[4-(3-di-n-propylaminopropyl)-oxy-3-chloro-benzoyl]-indolizine acid oxalate | 159–160 (methanol) |
| 1-Bromo-2-methyl-3-[4-(3-di-n-butylaminopropyl)-oxy-3-bromo-benzoyl]-indolizine acid oxalate | 89–90 (isopropanol) |
| 1-Bromo-2-methyl-3-[4-(3-di-n-propylaminopropyl)-oxy-3-bromo-benzoyl]-indolizine acid oxalate | 164–165 (isopropanol/ methanol) |
| 1-Bromo-2-ethyl-3-[4-(2-dimethylaminoethyl)-oxy-3-bromo-benzoyl]-indolizine acid oxalate | 164–165 (dichlorethane) |
| 1-Bromo-2-ethyl-3-[4-(3-dimethylaminopropyl)-oxy-3-bromo-benzoyl]-indolizine acid oxalate | 150–151 (dichlorethane) |
| 1-Bromo-2-ethyl-3-[4-(2-diethylaminoethyl)-oxy-3-bromo-benzoyl]-indolizine acid oxalate | 168–169 (dichlorethane) |
| 1-Bromo-2-ethyl-3-[4-(3-diethylaminopropyl)-oxy-3-bromo-benzoyl]-indolizine acid oxalate | 140–141.5 |

| Compounds | M.P. °C. |
|---|---|
| | (isopropanol) |
| 1-Bromo-2-ethyl-3-[4-(2-di-n-propylaminoethyl)-oxy-3-bromo-benzoyl]-indolizine acid oxalate | 163–164 (isopropanol) |
| 1-Bromo-2-ethyl-3-[4-(3-di-n-propylaminopropyl)-oxy-3-bromo-benzoyl]-indolizine acid oxalate | 139–140 (isopropanol) |
| 1-Bromo-2-ethyl-3-[4-(2-di-n-butylaminoethyl)-oxy-3-bromo-benzoyl]-indolizine acid oxalate | 164–165 (isopropanol) |
| 1-Bromo-2-ethyl-3-[4-(3-di-n-butylaminopropyl)-oxy-3-bromo-benzoyl]-indolizine acid oxalate | 101–101.5 (isopropanol) |
| 1-Bromo-2-n-propyl-3-[4-(3-di-n-butylaminopropyl)-oxy-3-bromo-benzoyl]-indolizine acid oxalate | 92 (benzene) |
| 1-Bromo-2-n-propyl-3-[4-(3-di-n-propylaminopropyl)-oxy-3-bromo-benzoyl]-indolizine acid oxalate | 132–136 (isopropanol) |
| 1-Bromo-2-n-butyl-3-[4-(3-di-n-propylaminopropyl)-oxy-3-bromo-benzoyl]-indolizine acid oxalate | 151–152 (2/1 isopropanol/ methanol) |
| 1-Bromo-2-n-butyl-3-[4-(3-di-n-butylaminopropyl)-oxy-3-bromo-benzoyl]-indolizine acid oxalate | 101–103 (isopropanol) |
| 1-Bromo-2-phenyl-3-[4-(3-di-n-propylaminopropyl)-oxy-3-bromo-benzoyl]-indolizine acid oxalate | 169–170 (1/1 methanol/isopropanol) |
| 1-Bromo-2-phenyl-3-[4-(3-di-n-butylaminopropyl)-oxy-3-bromo-benzoyl]-indolizine acid oxalate | 167–169 (isopropanol) |
| 1-Bromo-2-(4-methoxy-phenyl)-3-[4-(3-di-n-butylaminopropyl)-oxy-3-bromo-benzoyl]-indolizine acid oxalate | 178–179 (methanol) |
| 1-Bromo-2-(4-methyl-phenyl)-3-[4-(3-di-n-butylaminopropyl)-oxy-3-bromo-benzoyl]-indolizine acid oxalate | 169–170.5 (1/1 isopropanol/ (methanol) |
| 1-Bromo-2-(4-fluoro-phenyl)-3-[4-(3-di-n-butylaminopropyl)-oxy-3-bromo-benzoyl]-indolizine acid oxalate | 170–171 (methanol) |
| 1-Bromo-2-(3-bromo-phenyl)-3-[4-(3-di-n-butylaminopropyl)-oxy-3-bromo-benzoyl]-indolizine acid oxalate | 172–173 (methanol) |
| 1-Bromo-2-n-butyl-3-[4-(4-di-n-butylaminobutyl)-oxy-3-bromo-benzoyl]-indolizine acid oxalate | 118–120 (isopropanol) |
| 1-Chloro-2-ethyl-3-[4-(3-di-n-butylaminopropyl)-oxy-3-chloro-benzoyl]-indolizine acid oxalate | 115–117 (isopropanol) |
| 1-Chloro-2-ethyl-3-[4-(3-di-n-propylaminopropyl)-oxy-3-chloro-benzoyl]-indolizine acid oxalate | 137–138 (isopropanol) |
| 1-Chloro-2-(3-bromo-phenyl)-3-[4-(3-di-n-butylaminopropyl)-oxy-3-chloro-benzoyl]-indolizine acid oxalate | 171–172 (methanol) |
| 1-Chloro-2-(3-bromo-phenyl)-3-[4-(3-di-n-propylaminopropyl)-oxy-3-chloro-benzoyl]-indolizine acid oxalate | 194–195 (methanol) |
| 1-Chloro-2-ethyl-3-[4-(3-di-n-propylaminopropyl)-oxy-3,5-dichloro-benzoyl]-indolizine acid oxalate | 141 (ethyl acetate) |

-continued

| Compounds | M.P. °C. |
|---|---|
| 1-Chloro-2-ethyl-3-[4-(3-di-n-butylaminopropyl)-oxy-3,5-dichloro-benzoyl]-indolizine acid oxalate | 129 (ethyl acetate) |
| 1-Chloro-2-phenyl-3-[4-(3-di-n-propylaminopropyl)-oxy-3,5-dichloro-benzoyl]-indolizine acid oxalate | 156 (isopropanol) |
| 1-Chloro-2-phenyl-3-[4-(3-di-n-butylaminopropyl)-oxy-3,5-dichloro-benzoyl]dichloro-benzoyl]-indolizine acid oxalate | 136 (isopropanol/heptane) |
| 1-Bromo-2-methyl-3-[4-(3-di-n-propylaminopropyl)-oxy-3-chloro-benzoyl]-indolizine acid oxalate | 110–112 (isopropanol) |
| 1-Bromo-2-methyl-3-[4-(3-di-n-butylaminopropyl)-oxy-3-chloro-benzoyl]-indolizine acid oxalate | 108–110 (isopropanol) |
| 1-Bromo-2-ethyl-3-[4-(3-di-n-propylaminopropyl)-oxy-3-chloro-benzoyl]-indolizine acid oxalate | 136.5–138 (isopropanol) |
| 1-Bromo-2-ethyl-3-[4-(3-di-n-butylaminopropyl)-oxy-3-chloro-benzoyl]-indolizine acid oxalate | 103–105 (isopropanol) |
| 1-Bromo-2-n-propyl-3-[4-(3-di-n-butylaminopropyl)-oxy-3-chloro-benzoyl]-indolizine acid oxalate | 95–96 (isopropanol) |
| 1-Bromo-2-isopropyl-3-[4-(3-di-n-butylaminopropyl)-oxy-3-chloro-benzoyl]-indolizine acid oxalate | 116 (isopropanol) |
| 1-Bromo-2-n-butyl-3-[4-(3-di-n-propylaminopropyl)-oxy-3-chloro-benzoyl]-indolizine acid oxalate | 159–160 (methanol) |
| 1-Bromo-2-n-butyl-3-[4-(3-di-n-propylaminopropyl)-oxy-3-chloro-benzoyl]-indolizine acid oxalate | 101–103 (isopropanol) |
| 1-Bromo-2-phenyl-3-[4-(3-di-n-butylaminopropyl)-oxy-3-chloro-benzoyl]-indolizine acid oxalate | 167.5–169 (methanol) |
| 1-Bromo-2-phenyl-3-[4-(3-di-n-propylaminopropyl)-oxy-3-chloro-benzoyl]-indolizine acid oxalate | 169–170 (methanol) |
| 1-Bromo-2-(4-chloro-phenyl)-3-[4-(3-di-n-butylaminopropyl)-oxy-3-chloro-benzoyl]-indolizine acid oxalate | 160–161 (isopropanol) |
| 1-Bromo-2-(4-chloro-phenyl)-3-[4-(3-di-n-propylaminopropyl)-oxy-3-chloro-benzoyl]-indolizine acid oxalate | 184–185 (methanol) |
| 1-Bromo-2-(4-bromo-phenyl)-3-[4-(3-di-n-propylaminopropyl)-oxy-3-chloro-benzoyl]-indolizine acid oxalate | 176–177 (methanol) |
| 1-Bromo-2-(4-bromo-phenyl)-3-[4-(3-di-n-butylaminopropyl)-oxy-3-chloro-benzoyl]-indolizine acid oxalate | 168–169 (isopropanol) |
| 1-Bromo-2-(3-bromo-phenyl)-3-[4-(3-di-n-propylaminopropyl)-oxy-3-chloro-benzoyl]-indolizine acid oxalate | 200–201 (methanol) |
| 1-Bromo-2-(3-bromo-phenyl)-3-[4-(3-di-n-butylaminopropyl)-oxy-3-chloro-benzoyl]-indolizine acid oxalate | 170.5–172 (methanol) |
| 1-Chloro-2-ethyl-3-[4-(3-di-n-butylaminopropyl)-oxy-3-bromo-benzoyl]-indolizine acid oxalate | 104–105 (isopropanol) |
| 1-Chloro-2-ethyl-3-[4-(3-di-n-propylaminopro- | |

-continued

| Compounds | M.P. °C. |
|---|---|
| pyl)-oxy-3,5-dibromo-benzoyl]-indolizine acid oxalate | 157 (isopropanol) |
| 1-Chloro-2-ethyl-3-[4-(3-di-n-butylaminopropyl)-oxy-3,5-dibromo-benzoyl]-indolizine acid oxalate | 140 (isopropanol) |
| 1-Chloro-2-phenyl-3-[4-(3-di-n-propylaminopropyl)-oxy-3,5-dibromo-benzoyl]-indolizine acid oxalate | 172 (isopropanol) |
| 1-Chloro-2-phenyl-3-[4-(3-di-n-butylaminopropyl)-oxy-3,5-dibromo-benzoyl]-indolizine acid oxalate | 146 (isopropanol) |
| 2-Methyl-3-[4-(3-di-n-propylaminopropyl)-oxy-3,5-dibromo-benzoyl]-indolizine sesquioxalate | 136 (ethyl acetate) |
| 2-Ethyl-3-[4-(3-dimethylaminopropyl)-oxy-3,5-dibromo-benzoyl]-indolizine acid oxalate | 148 (ethyl acetate) |
| 2-Ethyl-3-[4-(2-diethylaminopropyl)-oxy-3,5-dibromo-benzoyl]-indolizine acid oxalate | 171 (ethanol) |
| 2-Ethyl-3-[4-(3-diethylaminopropyl)-oxy-3,5-dibromo-benzoyl]-indolizine hydrochloride | 191 (50/50 ethyl acetate/ acetone) |
| 2-Ethyl-3-[4-(3-di-n-propylaminopropyl)-oxy-3,5-dibromo-benzoyl]-indolizine hydrochloride | 166 (ethyl acetate) |
| 2-Ethyl-3-[4-(3-di-n-butylaminopropyl)-oxy-3,5-dibromo-benzoyl]-indolizine hydrochloride | 157 (ethyl acetate) |
| 2-n-Propyl-3-[4-(3-di-n-propylaminopropyl)-oxy-3,5-dibromo-benzoyl]-indolizine hydrochloride | 145 (ethyl acetate) |
| 2-n-Propyl-3-[4-(3-di-n-butylaminopropyl)-oxy-3,5-dibromo-benzoyl]-indolizine acid oxalate | 107 (ethyl acetate) |
| 2-Isopropyl-3-[4-(3-di-n-propylaminopropyl)-oxy-3,5-dibromo-benzoyl]-indolizine acid oxalate | 126 (ethyl acetate/ ethanol) |
| 2-Isopropyl-3-[4-(3-di-n-butylaminopropyl)-oxy-3,5-dibromo-benzoyl]-indolizine acid oxalate | 86 (ethyl acetate/ethyl ether) |
| 2-n-Butyl-3-[4-(3-di-n-propylaminopropyl)-oxy-3,5-dibromo-benzoyl]-indolizine acid oxalate | 146 (ethyl acetate) |
| 2-n-Butyl-3-[4-(3-di-n-butylaminopropyl)-oxy-3,5-dibromo-benzoyl]-indolizine acid oxalate | 110 (ethyl acetate) |
| 2-Phenyl-3-[4-(3-di-n-propylaminopropyl)-oxy-3,5-dibromo-benzoyl]-indolizine acid oxalate | 142 (ethyl acetate/ ethanol) |
| 2-Phenyl-3-[4-(3-di-n-butylaminopropyl)-oxy-3,5-dibromo-benzoyl]-indolizine acid oxalate | 86 (ethyl acetate) |
| 2-(4-Fluoro-phenyl)-3-[4-(3-di-n-propylaminopropyl)-oxy-3,5-dibromo-benzoyl]-indolizine acid oxalate | 166 (ethyl acetate/ ethanol) |
| 2-(4-Fluoro-phenyl)-3-[4-(3-di-n-butylaminopropyl)-oxy-3,5-dibromo-benzoyl]-indolizine acid oxalate | 152 (isopropanol) |

-continued

| Compounds | M.P. °C. |
|---|---|
| 2-(4-Chloro-phenyl)-3-[4-(3-di-n-propylaminopropyl)-oxy-3,5-dibromo-benzoyl]-indolizine acid oxalate | 190 (ethyl acetate) |
| 2-(4-Chloro-phenyl)-3-[4-(3-di-n-butylaminopropyl)-oxy-3,5-dibromo-benzoyl]-indolizine acid oxalate | 88 (ethyl acetate) |
| 2-(3,4-Dichloro-phenyl)-3-[4-(3-di-n-propylaminopropyl)-oxy-3,5-dibromo-benzoyl]-indolizine sesquioxalate | 114 (ethyl acetate/isopropanol) |
| 2-(3,4-Dichloro-phenyl)-3-[4-(3-di-n-butylaminopropyl)-oxy-3,5-dibromo-benzoyl]-indolizine acid oxalate | 95 (ethyl acetate/isopropanol) |
| 2-(3-Bromo-phenyl)-3-[4-(3-di-n-propylaminopropyl)-oxy-3,5-dibromo-benzoyl]-indolizine acid oxalate | 136 (ethanol) |
| 2-(3-Bromo-phenyl)-3-[4-(3-di-n-butylaminopropyl)-oxy-3,5-dibromo-benzoyl]-indolizine acid fumurate | 122 (ethyl acetate) |
| 2-(4-Methyl-phenyl)-3-[4-(3-di-n-propylaminopropyl)-oxy-3,5-dibromo-benzoyl]-indolizine acid oxalate | 126 (ethyl acetate/isopropanol) |
| 2-(4-Methyl-phenyl)-3-[4-(3-di-n-butylaminopropyl)-oxy-3,5-dibromo-benzoyl]-indolizine acid oxalate | 90 (ethyl acetate) |
| 2-(4-Methoxy-phenyl)-3-[4-(3-di-n-propylaminopropyl)-oxy-3,5-dibromo-benzoyl]-indolizine acid oxalate | 167 (acetone) |
| 2-(4-Methoxy-phenyl)-3-[4-(3-di-n-butylaminopropyl)-oxy-3,5-dibromo-benzoyl]-indolizine acid oxalate | pasty at about 70° C. (ethanol/ethyl ether) |
| 2-Methyl-3-[4-(3-di-n-propylaminopropyl)-oxy-3,5-dichloro-benzoyl]-indolizine acid oxalate | 145 (ethyl acetate/ethanol) |
| 2-Methyl-3-[4-(3-di-n-butylaminopropyl)-oxy-3,5-dichloro-benzoyl]-indolizine acid oxalate | 95 (ethyl acetate/ethyl ether) |
| 2-Ethyl-3-[4-(3-di-n-propylaminopropyl)-oxy-3,5-dichloro-benzoyl]-indolizine acid oxalate | 100 (pasty) (ethyl acetate) |
| 2-Ethyl-3-[4-(3-di-n-butylaminopropyl)-oxy-3,5-dichloro-benzoyl]-indolizine acid oxalate | 95 (ethyl acetate) |
| 2-n-Propyl-3-[4-(3-di-n-propylaminopropyl)-oxy-3,5-dichloro-benzoyl]-indolizine acid oxalate | 142 (isopropanol) |
| 2-n-Propyl-3-[4-(3-di-n-butylaminopropyl)-oxy-3,5-dichloro-benzoyl]-indolizine acid oxalate | 114 (isopropanol) |
| 2-Isopropyl-3-[4-(3-di-n-propylaminopropyl)-oxy-3,5-dichloro-benzoyl]-indolizine acid oxalate | 86 (ethyl acetate) |
| 2-Isopropyl-3-[4-(3-di-n-butylaminopropyl)-oxy-3,5-dichloro-benzoyl]-indolizine acid oxalate | 90 (ethyl acetate) |
| 2-Phenyl-3-[4-(3-di-n-propylaminopropyl)-oxy-3,5-dichloro-benzoyl]-indolizine acid oxalate | 146 (ethanol) |
| 2-Phenyl-3-[4-(3-di-n-butylaminopropyl)-oxy-3,5-dichloro-benzoyl]-indolizine | |

-continued

| Compounds | M.P. °C. |
|---|---|
| acid oxalate | pasty at about 90° C. (ethyl acetate) |
| 2-(4-Bromo-phenyl)-3-[4-(3-di-n-propyl-aminopropyl)-oxy-3,5-dichloro-benzoyl]-indolizine acid oxalate | 174 (ethyl acetate) |
| 2-(4-Bromo-phenyl)-3-[4-(3-di-n-butyla-minopropyl)-oxy-3,5-dichloro-benzoyl]-indolizine acid oxalate | 133 (ethyl acetate) |
| 1-Bromo-2-methyl-3-[4-(3-di-n-butyla-minopropyl)-oxy-3,5-dibromo-benzoyl]-indolizine acid oxalate | 141–143 (isopropanol) |
| 1-Bromo-2-n-propyl-3-[4-(3-di-n-propyla-minopropyl)-oxy-3,5-dibromo-benzoyl]-indolizine acid oxalate | 138–139 (isopropanol) |
| 1-Bromo-2-ethyl-3-[4-(3-di-n-butylamino-propyl)-oxy-3,5-dibromo-benzoyl]-indoli-zine acid oxalate | 131–132.5 (isopropanol) |
| 1-Bromo-2-phenyl-3-[4-(3-di-n-butylamino-propyl)-oxy-3,5-dibromo-benzoyl]-indoli-zine acid oxalate | 160–161 (isopropanol) |
| 1-Bromo-2-(4-methyl-phenyl)-3-[4-(3-di-n-butylaminopropyl)-oxy-3,5-dibromo-benzoyl]-indolizine acid oxalate | 105–106 (isopropanol) |
| 1-Bromo-2-(4-bromo-phenyl)-3-[4-(3-di-n-butylaminopropyl)-oxy-3,5-dibromo-benzoyl]-indolizine acid oxalate | 148–149 (isopropanol) |
| 1-Bromo-2-(3,4-dichloro-phenyl)-3-[4-(3-di-n-butylaminopropyl)-oxy-3,5-dibromo-ben-zoyl]-indolizine acid oxalate | 196–197 (isopropanol) |
| 1-Bromo-2-(3-chloro-4-methyl-phenyl)-3-[4-(3-di-n-butylaminopropyl)-oxy-3,5-dibromo-benzoyl]-indolizine acid oxalate | 168–169 (isopropanol) |
| 1-Bromo-2-ethyl-3-[4-(3-di-n-butylaminopro-pyl)-oxy-3,5-dichloro-benzoyl]-indolizine acid oxalate | 134 (isopropanol) |
| 1-Bromo-2-phenyl-3-[4-(3-di-n-propylamino-propyl)-oxy-3,5-dichloro-benzoyl]-indolizine acid oxalate | 145 (ethyl acetate) |
| 1-Bromo-2-phenyl-3-[4-(3-di-n-butylamino-propyl)-oxy-3,5-dichloro-benzoyl]-indolizine acid oxalate | 106 (ethyl acetate) |
| 2-n-Butyl-3-[4-(3-di-n-butylaminopropyl)-oxy-3-bromo-benzoyl]-indolizine hydrochloride | 113–113.5 (ethyl acetate) |
| 2-n-Propyl-3-[4-(3-diethyl-aminopropyl)-oxy-3,5-dibromo-benzoyl]-indolizine hydrochloride | 154 (80/20 ethyl acetate/ acetone) |
| 2-Ethyl-3-[4-(3-di-n-butylaminopropyl)-oxy-3-chloro-benzoyl]-indolizine hydrochloride | 132–133 (ethyl acetate/isopropa-nol) |
| 2-n-Butyl-3-[4-(3-di-n-butylaminopropyl)-oxy-3-chloro-benzoyl]-indolizine hydrochloride | 104 (ethyl acetate) |
| 1-Bromo-2-phenyl-3-[4-(3-di-n-butylaminopropyl)-oxy-3-chloro-benzoyl]-indolizine hydrochloride | 156–157 |
| 1-Chloro-2-(4-chloro-phenyl)-3-[ 4-(3-di-n-propyl-aminopropyl)-oxy-benzoyl]-indolizine acid oxalate | 168–169 (methanol) |
| 1-Methoxy-2-phenyl-3-[4-(3-di-n-propylaminopropyl)-oxy-benzoyl]-indolizine acid oxalate | 117 (ethyl acetate) |
| 1-Methoxy-2-phenyl-3-[4-(3-di-n-butylaminopropyl)-oxy-benzoyl]-indolizine acid oxalate | 80 (ethyl acetate) |
| 1-Methoxy-2-phenyl-3-[4-(3-di-n-propylaminopropyl)-oxy-3-chloro-benzoyl]-indolizine acid oxalate | 172 |

-continued

| Compounds | M.P. °C. |
|---|---|
| 1-Methoxy-2-phenyl-3-[4-(3-di-n-butylaminopropyl)-oxy-3-chloro-benzoyl]-indolizine acid oxalate | (ethyl acetate)<br>120<br>(ethyl acetate) |
| 1-Methoxy-2-phenyl-3-[4-(3-di-n-propylaminopropyl)-oxy-3-bromo-benzoyl]-indolizine acid oxalate | 160<br>(ethyl acetate) |
| 1-Methoxy-2-phenyl-3-[4-(3-di-n-butylaminopropyl)-oxy-3-bromo-benzoyl]-indolizine acid oxalate | 78<br>(ethyl acetate) |
| 1-Methoxy-2-phenyl-3-[4-(3-di-n-propylaminopropyl)-oxy-3-methoxy-benzoyl]-indolizine acid oxalate | 148<br>(ethyl acetate) |
| 1-Methoxy-2-phenyl-3-[4-(3-di-n-butylaminopropyl)-oxy-3-methoxy-benzoyl]-indolizine acid oxalate | 78<br>(ethyl acetate) |
| 1-Methoxy-2-(4-fluoro-phenyl)-3-[4-(3-di-n-propylaminopropyl)-oxy-3-methoxy-benzoyl]-indolizine acid oxalate | 79<br>(ethyl acetate) |
| 2-Methyl-3-[4-(3-di-n-butylaminopropyl)-oxy-3-methoxy-benzoyl]-indolizine acid oxalate | 159<br>(isopropanol) |
| 2-Methyl-3-[4-(3-di-n-propylaminopropyl)-oxy-3-methoxy-benzoyl]-indolizine acid oxalate | 171<br>(methanol) |
| 2-Ethyl-3-[4-(3-di-n-butylaminopropyl)-oxy-3-methoxy-benzoyl]-indolizine acid oxalate | 88<br>(ethyl acetate) |
| 2-Ethyl-3-[4-(3-di-n-propylaminopropyl)-oxy-3-methoxy-benzoyl]-indolizine acid oxalate | 121–122<br>(ethyl acetate) |
| 1-Bromo-2-methyl-3-[4-(3-di-n-butylaminopropyl)-oxy-3-methoxy-benzoyl]-indolizine acid oxalate | 87–90<br>(benzene) |
| 1-Bromo-2-methyl-3-[4-(3-di-n-propylaminopropyl)-oxy-3-methoxy-benzoyl]-indolizine acid oxalate | 139–141<br>(isopropanol) |
| 1-Bromo-2-ethyl-3-[4-(3-di-n-butylaminopropyl)-oxy-3-methoxy-benzoyl]-indolizine acid oxalate | 111<br>(benzene) |
| 1-Bromo-2-ethyl-3-[4-(3-di-n-propylaminopropyl)-oxy-3-methoxy-benzoyl]-indolizine acid oxalate | 149<br>(isopropanol) |
| 2-(4-Fluoro-phenyl)-3-[4-(3-di-n-butylaminopropyl)-oxy-3-methoxy-benzoyl]-indolizine acid oxalate | 85<br>(ethyl acetate) |
| 2-Methyl-3-[4-(3-di-n-butylaminopropyl)-oxy 3-methyl-benzoyl]-indolizine acid oxalate | 149<br>(isopropanol) |
| 2-Ethyl-3-[4-(3-di-n-butylaminopropyl)-oxy-3-methyl-benzoyl]-indolizine acid oxalate | 133<br>(ethyl acetate) |
| 1-Methyl-2-n-propyl-3-[4-(3-di-n-butylaminopropyl)-oxy-3-bromo-benzoyl]-indolizine acid oxalate | 127<br>(ethyl acetate) |
| 2-Isopropyl-3-[4-(3-di-n-butylaminopropyl)-oxy-3-methyl-benzoyl]-indolizine acid oxalate | 91<br>(isopropanol) |
| 2-n-Butyl-3-[4-(3-di-n-butylaminopropyl)-oxy-3-methyl-benzoyl]-indolizine acid oxalate | 89<br>(isopropanol) |
| 1-Methyl-2-n-butyl-3-[4-(3-di-n-butylaminopropyl)-oxy-3-bromo-benzoyl]-indolizine acid oxalate | 99<br>(ethyl acetate) |
| 1-Methyl-2-ethyl-3-[4-(3-di-n-butylaminopropyl)-oxy-3-bromo-benzoyl]-indolizine acid oxalate | 117<br>(ethyl acetate) |
| 1-Bromo-2-methyl-3-[4-(3-di-n-butylaminopropyl)-oxy-3,5-dimethyl-benzoyl]-indolizine acid oxalate | 120–122<br>(isopropanol) |
| 1-Iodo-2-ethyl-3-[4-(3-di-n-butylaminopropyl)-oxy-3,5-dimethyl-benzoyl]-indolizine acid oxalate | 115<br>(ethyl acetate) |
| 2-Ethyl-3-[2,3-dichloro-4-(3-di-n-propylamino-propyl)-oxy-benzoyl]-indolizine | 117<br>(heptane) |
| 2-Ethyl-3-[2,3-dichloro-4-(3-di-n-butylamino-propyl)-oxy-benzoyl]-indolizine | 95<br>(heptane) |
| 2-Phenyl-3-[2,3-dichloro-4-(3-di-n-propylamino- | |

-continued

| Compounds | M.P. °C. |
|---|---|
| propyl)-oxy-benzoyl]-indolizine | 99 (heptane) |
| 2-Phenyl-3-[2,3-dichloro-4-(3-di-n-butylamino-propyl)-oxy-benzoyl]-indolizine | 87 (heptane) |
| 2-(4-Fluoro-phenyl)-3-[2,3-dichloro-4-(3-di-n-propylaminopropyl)-oxy-benzoyl]9 -indolizine | 119 (heptane) |
| 2-(4-Fluoro-phenyl)-3-[2,3-dichloro-4-(3-di-n-butylaminopropyl)-oxy-benzoyl]-indolizine | 95-96 (heptane) |
| 1-Bromo-2-ethyl-3-[2,3-dichloro-4-(3-di-n-butylaminopropyl)-oxy-benzoyl]-indolizine acid oxalate | 164 (isopropanol) |
| 1-Bromo-2-phenyl-3-[2,3-dichloro-4-(3-di-n-propylaminopropyl)-oxy-benzoyl]-indolizine acid oxalate | 171 (isopropanol) |
| 1-Chloro-2-phenyl-3-[2,3-dichloro-4-(3-di-n-propylaminopropyl)-oxy-benzoyl]-indolizine | 136 (heptane) |
| 2-n-Butyl-3-[4-(3-di-n-butylaminopropyl)-oxy-3-iodo-benzoyl]-indolizine acid oxalate | 90-92 (ethyl acetate) |

EXAMPLE 5

In accordance with known pharmaceutical techniques soft-gelatin capsules containing the following ingredients, were prepared:

| Ingredient | mg |
|---|---|
| 2-n-Butyl-3-[4-(3-di-n-butylaminopropyl)-oxy-3-bromo/or 3-chloro-benzoyl]-indolizine hydrochloride | 100 |
| Starches | 99.5 |
| Colloidal silica | 0.5 |
| | 200.0 |

EXAMPLE 6

In accordance with known pharmaceutical techniques, injectable solutions containing the following ingredients, were prepared:

| Ingredient | mg |
|---|---|
| 2-n-Butyl-3-[4-(3-di-n-butylaminopropyl)-oxy-3-bromo/or 3-chloro-benzoyl]-indolizine hydrochloride | 150 |
| Polysorbate 80 | 150 |
| Benzyl alcohol | 75 |
| Water to 3 ml | |

EXAMPLE 7

In accordance with known pharmaceutical techniques, suppositories containing the following ingredients, were prepared:

| Ingredient | mg |
|---|---|
| 2-n-Butyl-3-[4-(3-di-n-butylaminopropyl)-oxy-3-bromo/or 3-chloro-benzoyl]-indolizine hydrochloride | 100 |
| Mixture of mono- and di-glycerides of saturated acids ($C_{12}$ to $C_{18}$) | 1400 |
| | 1500 |

We claim:
1. An indolizine compound corresponding to the formula:

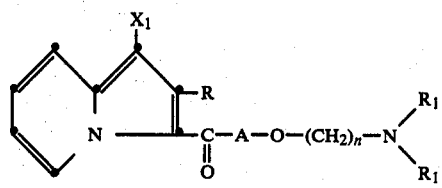

and pharmaceutically acceptable acid addition salts thereof wherein:

R represents a branched- or straight-chain alkyl radical having from 1 to 8 carbon atoms, or a phenyl group non-substituted or bearing one or two substituents, which may be the same or different selected from halogen atoms and from lower alkyl and alkoxy groups, $X_1$ represents hydrogen, chlorine, bromine, iodine, or methoxy, A represents a group selected from:

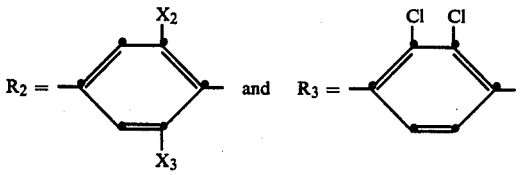

in which $X_2$ represents hydrogen, chlorine, bromine, iodine, or methoxy and $X_3$ represents hydrogen, chlorine, bromine, or iodine, $R_1$ represents a methyl, ethyl, n-propyl or n-butyl radical, n represents an integer in the range of 2 to 6 inclusive with the proviso that when both $X_2$ and $X_3$ represent hydrogen, $X_1$ is halogen or methoxy.

2. An indolizine derivative according to claim 1 wherein R represents a branched- or straight-chain alkyl radical having from 1 to 8 carbon atoms, a phenyl radical, a mono-fluoro-, mono-chloro-, mono-bromo-, or mono-methoxy-phenyl radical, a di-fluoro-, di-chloro-, di-bromo-phenyl radical or a methyl-phenyl radical substituted in the aromatic moiety by an atom of fluorine, chlorine or bromine.

3. 1-Bromo-2-methyl-3-[4-(3-di-n-butylaminopropyl)-oxy-3-bromo-benzoyl]-indolizine and pharmaceutically acceptable acid addition salts thereof.

4. 2-n-Butyl-3-[4-(3-di-n-butylaminopropyl)-oxy-3-bromo-benzoyl]-indolizine and pharmaceutically acceptable acid addition salts thereof.

5. 2-Ethyl-3-[4-(3-di-n-butylaminopropyl)-oxy-3-chloro-benzoyl]-indolizine and pharmaceutically acceptable acid addition salts thereof.

6. 2-n-Butyl-3-[4-(3-di-n-butylaminopropyl)-oxy-3-chloro-benzoyl]-indolizine and pharmaceutically acceptable acid addition salts thereof.

7. 2-Isopropyl-3-[4-(3-di-n-butylaminopropyl)-oxy-3,5-dichloro-benzoyl]-indolizine and pharmaceutically acceptable acid addition salts thereof.

8. 1-Bromo-2-phenyl-3-[4-(3-di-n-butylaminopropyl)-oxy-3-chloro-benzoyl]-indolizine and pharmaceutically acceptable acid addition salts thereof.

9. 1-Chloro-2-ethyl-3-[4-(3-di-n-butylaminopropyl)-oxy-3-chloro-benzoyl]-indolizine and pharmaceutically acceptable acid addition salts thereof.

10. 1-Chloro-2-n-butyl-3-[4-(3-di-n-butylaminopropyl]-oxy-benzoyl]-indolizine and pharmaceutically acceptable acid addition salts thereof.

11. 1-Bromo-2-(4-chloro-phenyl)-3-[4-(3-di-n-butylaminopropyl)-oxy-3-chloro-benzoyl]-indolizine and pharmaceutically acceptable acid addition salts thereof.

12. An indolizine derivative according to any of claims 1, 2, 3, 4, 5, 6, 7, 8, 9, 10 or 11 wherein the pharmaceutically acceptable acid addition salt is the hydrochloride or the acid oxalate.

13. A pharmaceutical or veterinary composition containing as active principle at least one indolizine derivative or pharmaceutically acceptable acid addition salt according to claim 1 or 2, in association with a pharmaceutical carrier or excipient therefor.

14. A pharmaceutical or veterinary composition containing as active principle at least one indolizine derivative or pharmaceutically acceptable acid addition salt according to any of claims 3, 4, 5, 6, 7, 8, 9, 10 or 11 in association with a pharmaceutical carrier or excipient therefor.

15. A method of treating pathological syndromes of the heart and particularly angina pectoris and cardiac arrhythmias in a subject needing such treatment, which method comprises administering to said subject an effective dose of at least one indolizine derivative according to claims 1 or 2.

16. A method of treating pathological syndromes of the heart and particularly angina pectoris and cardiac arrhythmias in a subject needing such treatment, which method comprises administering to said subject an effective dose of at least one indolizine derivative according to any of claims 3, 4, 5, 6, 7, 8, 9, 10 or 11.

17. A method according to claim 15 wherein the effective dose is 100 to 300 mg by oral route or 1 to 3 mg by parenteral route per day to a subject weighing 60 kgs.

18. 1-Bromo-2-n-butyl-3-[4-(3-di-n-butylaminopropyl)-oxy-3-chlorobenzoyl]-indolizine and pharmaceutically acceptable acid addition salts thereof.

* * * * *

UNITED STATES PATENT AND TRADEMARK OFFICE
CERTIFICATE OF CORRECTION

PATENT NO. : 4,378,362
DATED : March 29, 1983
INVENTOR(S) : Gilbert Rosseels, et al.

It is certified that error appears in the above—identified patent and that said Letters Patent are hereby corrected as shown below:

Title page first column, after item [22], insert the following:

-- [30] Foreign Application Priority Data

Dec. 6, 1979 [BR] United Kingdom 79 42146 --

Signed and Sealed this

Twenty-first Day of June 1983

[SEAL]

Attest:

DONALD J. QUIGG

Attesting Officer    Acting Commissioner of Patents and Trademarks

UNITED STATES PATENT AND TRADEMARK OFFICE
CERTIFICATE OF CORRECTION

PATENT NO. : 4,378,362
DATED : March 29, 1983
INVENTOR(S) : Gilbert Rosseels, et al.

It is certified that error appears in the above–identified patent and that said Letters Patent are hereby corrected as shown below:

Col. 4, line 31, change "British" to -- U.S. --

Col. 4, line 44, change "British" to -- U.S. --

Col. 4, line 67, change "British" to -- U.S. --

Col. 5, line 4, change "British" to -- U.S. --

Signed and Sealed this

Twenty-sixth Day of July 1983.

[SEAL]

Attest:

Attesting Officer

GERALD J. MOSSINGHOFF

Commissioner of Patents and Trademarks